United States Patent [19]

Eriksson et al.

[11] 4,105,768

[45] Aug. 8, 1978

[54] HYPOTENSIVE SUBSTITUTED 1,2,4-TRIAZOLES

[75] Inventors: Hans Erik Eriksson, Sundsvall; Gösta Lennart Florvall, Södertälje, both of Sweden

[73] Assignee: Astra Läkemedel Aktiebolag, Södertälje, Sweden

[21] Appl. No.: 779,582

[22] Filed: Mar. 21, 1977

Related U.S. Application Data

[60] Continuation-in-part of Ser. No. 637,664, Dec. 4, 1975, abandoned, which is a division of Ser. No. 478,228, Jun. 11, 1974, Pat. No. 3,959,476, and a continuation-in-part of Ser. No. 635,140, Nov. 25, 1975, Pat. No. 4,022,905.

[30] Foreign Application Priority Data

Jun. 14, 1973 [SE] Sweden .............................. 7308365
Dec. 11, 1974 [NO] Norway .......................... 744468/74

[51] Int. Cl.² .................... A61K 31/44; C09B 23/16; C09B 55/00
[52] U.S. Cl. ................................. 424/263; 542/417
[58] Field of Search ....................... 424/263; 542/417

[56] References Cited

U.S. PATENT DOCUMENTS

| | | | |
|---|---|---|---|
| 3,516,995 | 6/1970 | Houlihan et al. | 260/240 G |
| 3,528,969 | 9/1970 | Houlihan et al. | 260/240 G |
| 3,769,278 | 10/1973 | Pifferi | 260/240 G |
| 3,775,405 | 11/1973 | Bruce | 260/240 G |
| 3,850,915 | 11/1974 | Bruce | 260/240 G |

*Primary Examiner*—Leonard Schenkman
*Attorney, Agent, or Firm*—Brumbaugh, Graves, Donohue & Raymond

[57] ABSTRACT

Compounds having the general formula

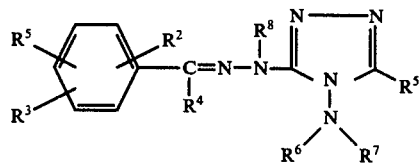

pharmaceutical preparations containing the compounds and use in the treatment of hypertension.

12 Claims, No Drawings

HYPOTENSIVE SUBSTITUTED 1,2,4-TRIAZOLES

This application is a continuation-in-part of our application Ser. No. 637,664, filed Dec. 4, 1975 now abandoned, which is a division of application Ser. No. 478,228, filed June 11, 1974, now U.S. Pat. No. 3,959,476, issued May 25, 1976. This application is also a continuation-in-part of our application Ser. No. 635,140, filed Nov. 25, 1975 now U.S. Pat. No. 4,022,905.

This invention relates to new triazoles and methods for their preparation. The invention also relates to the preparation of pharmaceutical preparations containing the triazoles and to methods for the pharmacological use of the triazoles.

PRIOR ART

Hypotensive agents have been known for a considerable time. It has also been known that these agents exert their effects through different mechanisms of action. Side-effects which have clinical implications of major importance are frequently encountered among these compounds. A well-known example is a rise in the blood pressure of shorter or longer duration after administration and before the onset of the desired fall in blood pressure. A further example is the sedative effect of these agents which may make these agents unsuitable for use by persons who perform any task which requires alertness, for instance car-driving.

OUTLINE OF INVENTION

(a) General Outline

We have found that certain compounds related to 4-amino-3-benzylidenehydrazino-1, 2, 4-triazoles have the ability of lowering the arterial blood pressure of unanesthetized animals with experimentally induced hypertension in oral doses which do not produce sedation or other apparent untoward effects.

More particularly, these compounds have the general formula

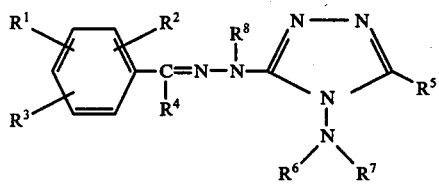

wherein $R^1$, $R^2$ and $R^3$ are the same or different and each represents a hydrogen atom, a lower alkyl group or a halogen atom, $R^4$ represents a hydrogen atom, a lower alkyl group or a pyridyl group, and $R^5$, $R^6$, $R^7$ and $R^8$ are the same or different and each represents a hydrogen atom or a lower alkyl group, provided that $R^4$ is a lower alkyl group or a pyridyl group when $R^1$, $R^2$ and $R^3$ are hydrogen atoms.

Included among these compounds are those of the formula I and having the above-defined substituents wherein $R^6$, $R^7$ and $R^8$ are not all simultaneously hydrogen atoms.

The invention also comprises pharmaceutically acceptable salts of the compounds of the formula I.

Illustrative examples of radicals included in the above definitions are pyridyl group: 2-pyridyl lower alkyl group: methyl, ethyl, n-propyl and iso-propyl halogen atom: chlorine, bromine, iodine and fluorine.

By the expression "lower alkyl group" in this application is to be understood alkyl groups with 1, 2 or 3 carbon atoms.

The table below gives some compounds within the scope of this application:

| $R^1$ | $R^2$ | $R^3$ | $R^6$ | $R^7$ | $R^8$ |
|---|---|---|---|---|---|
| 2—Cl | 6—Cl | H | $CH_3$ | H | H |
| 2—Cl | 6—Cl | H | $CH_3$ | $CH_3$ | H |
| 2—Cl | 6—Cl | H | $CH_3$ | $CH_3$ | $CH_3$ |
| 2—Cl | 6—Br | H | H | $CH_3$ | H |
| 2—Cl | 6—Br | H | $CH_3$ | $CH_3$ | H |
| 2—Cl | 6—Br | H | $CH_3$ | $CH_3$ | $CH_3$ |
| 2—Cl | 6—Cl | 4—$CH_3$ | $CH_3$ | H | H |
| 2—Cl | 6—Cl | 4—$CH_3$ | $CH_3$ | $CH_3$ | H |
| 2—Cl | 6—Cl | 4—$CH_3$ | $CH_3$ | $CH_3$ | $CH_3$ |
| 2—Cl | 6—$CH_3$ | 4—Cl | $CH_3$ | H | H |
| 2—Cl | 6—$CH_3$ | 4—Cl | $CH_3$ | $CH_3$ | H |
| 2—Cl | 6—$CH_3$ | 4—Cl | $CH_3$ | $CH_3$ | $CH_3$ |

An illustrative example of a compound of the formula I wherein $R^4$ is a lower alkyl group is 4-amino-3-(1-phenylethylidenehydrazino)-1, 2, 4-triazole.

(b) Pharmaceutical Preparations

In clinical practice the compounds of the present invention will normally be administered orally, rectally or by injection, in the form of pharmaceutical preparations comprising the active ingredient either as a free base or as a pharmaceutically acceptable non-toxic, acid addition salt, e.g. the hydrochloride, hydrobromide, lactate, acetate, sulphate, sulphamate, and the like, in association with a pharmaceutically acceptable carrier. Accordingly, terms relating to the novel compounds of this invention whether generically or specifically are intended to include both the free amine base and the acid addition salts of the free base, unless the context in which such terms are used, e.g. in the specific examples would be inconsistent with the broad concept. The carrier may be a solid, semisolid or liquid diluent or capsule. These pharmaceutical preparations constitute a further aspect of this invention. Usually the active substance will constitute between 0.1 and 95% by weight of the preparation, more specifically between 0.5 and 20% by weight for preparations intended for injection and between 2 and 50% by weight for preparations suitable for oral administration.

To produce pharmaceutical preparations containing a compound of the invention in the form of dosage units for oral application, the selected compound may be mixed with a solid pulverulent carrier, e.g. lactose, saccharose, sorbitol, mannitol, starches such as potato starch, corn starch or amylopectin, cellulose derivatives, or gelatine, and a lubricant such as magnesium stearate, calcium stearate, polyethylene glycol waxes, and the like, and then compressed to form tablets. If coated tablets are required, the cores, prepared as described above, may be coated with a concentrated sugar solution which may contain e.g. gum arabic, gelatine, talcum, titanium dioxide, and the like. Alternatively, the tablet can be coated with a lacquer dissolved in a readily volatile organic solvent or mixture of organic solvents. Dyestuffs may be added to these coatings in order to readily distinguish between tablets containing different active substances or different amounts of the active compound.

For the preparation of soft gelatine capsules (pearl-shaped closed capsules) consisting of gelatine, and for example, glycerol or similar closed capsules, the active substance may be admixed with a vegetable oil. Hard gelatine capsules may contain granulates of the active substance in combination with solid, pulverulent carriers such as lactose, saccharose, sorbitol, mannitol, starches (e.g. potato starch, corn starch or amylopectin), cellulose derivatives or gelatine.

Dosage units for rectal application can be prepared in the form of suppositories comprising the active substance in admixture with a neutral fatty base, or gelatine rectal capsules comprising the active substance in admixture with vegetable oil or paraffin oil.

Liquid preparations for oral application may be in the form of syrups or suspensions; for example, solutions containing from about 0.2 to about 20% by weight of the active substance herein described, the balance being sugar and a mixture of ethanol, water, glycerol, and propyleneglycol. Optionally such liquid preparations may contain coloring agents, flavoring agents, saccharine and carboxymethylcellulose as a thickening agent.

Solutions for parenteral applications by injection can be prepared in an aqueous solution of a water-soluble pharmaceutically acceptable salt of the active substance preferably in a concentration of from about 0.5 to about 10% by weight. These solutions may also contain stabilizing agents and/or buffering agents and may conveniently be provided in various dosage unit ampoules.

In therapeutical treatment the suitable diurnal doses of the compounds of the invention are dependent on such factors as, for instance, age and size of the patient and ways of administration.

(c) Preferred Embodiment

The preferred compounds of the invention have the structural formula

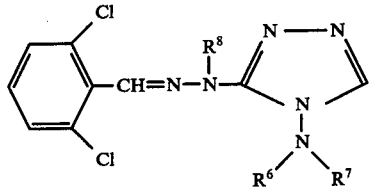

wherein $R^6$ is a hydrogen atom or a methyl group, $R^7$ is a hydrogen atom or a methyl group and $R^8$ is a hydrogen atom or a methyl group.

The compound of the formula

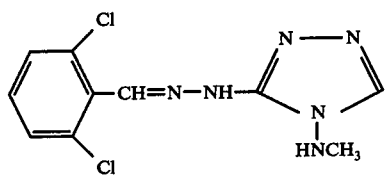

is particularly interesting.

Preferably these compounds will be prepared and used in the form of their hydrochloride salts.

(d) Methods of Preparation

A. Generally the compounds of the formula I where $R^1$, $R^2$, $R^3$, $R^4$, $R^5$, $R^6$, $R^7$ and $R^8$ have the above given difinitions, except that $R^6$, $R^7$ and $R^8$ are not all simultaneously hydrogen, are prepared via the following route:

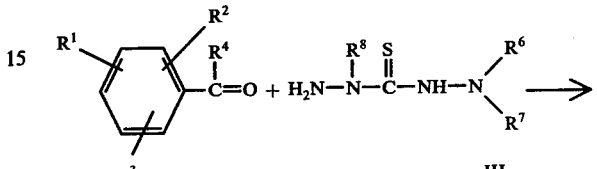

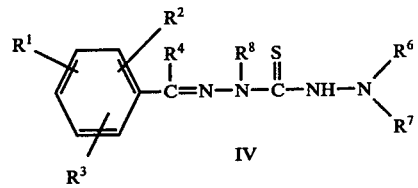

Substituted monothiocarbohydrazones of the formula IV are prepared by treating aldehydes or ketones of the formula II with a thiocarbohydrazide of the formula III. The reaction is preferably performed at elevated temperatures in a suitable solvent e.g. ethanol or acetic acid.

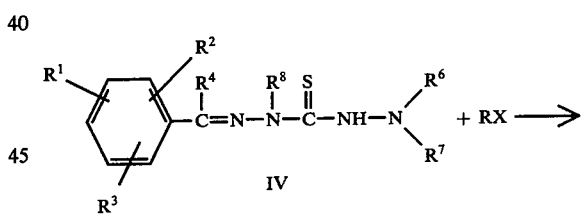

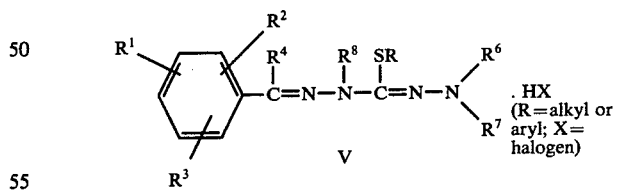

The substituted monothiocarbohydrazones IV are transformed into S-alkylisothiocarbohydrazones V by means of a halide or a dialkylsulphate such as methyl iodide, ethyl iodide, dimethyl sulphate, benzyl chloride and the like.

The reaction may be conducted in solvents such as ethanol from about room temperature to reflux temperature. The addition salt of V may be converted to the free base using conventional techniques, such as treating the salt with sodium carbonate solution.

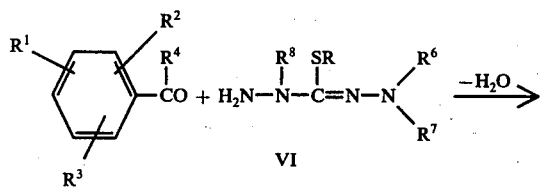

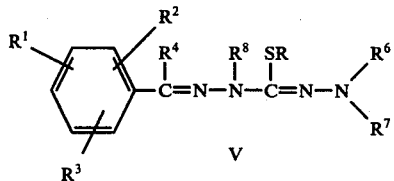

Alternatively, the S-alkylisothiocarbohydrazones can also be prepared from the corresponding aldehydes or ketones and a properly substituted S-alkylisothiocarbohydrazide VI. The reaction is performed as for the monothiocarbohydrazones.

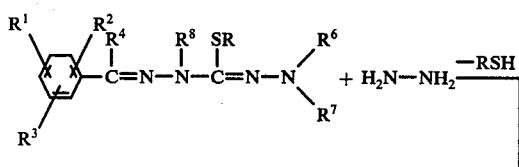

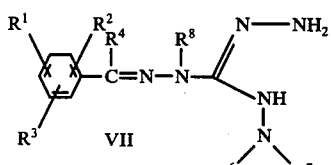

The addition salts or the free bases of the S-alkylisothiocarbohydrazones V are reacted with hydrazine or N, N-dialkylhydrazines yielding substituted 1-benzylideneamino-2,3-diaminoguanidines VII. The reaction may be conducted in solvents such as alcohols or in aqueous mixtures thereof. The products may be recovered using conventional techniques, such as filtration. The acid addition salts may be obtained from the free base by salifying.

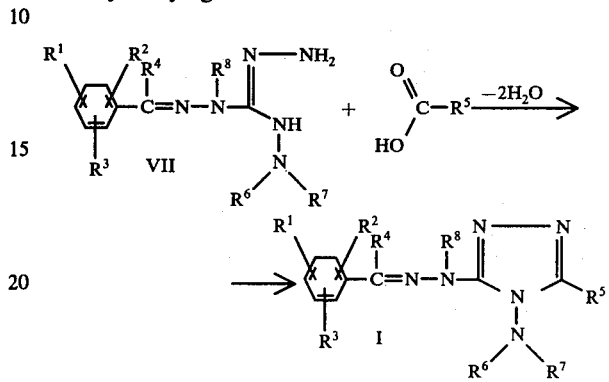

Compounds of the formula I wherein $R^6$, $R^7$ and $R^8$ are not all simultaneously hydrogen are prepared from the substituted 1-benzylideneamino-2,3-diaminoguanidines VII by reaction with carboxylic acids at elevated temperatures. The obtained 4-amino-3-benzylidenehydrazino-1, 2, 4-triazoles are preferably isolated as the addition salts, e.g. the hydrochlorides.

The intermediate compounds of formula III and VI are known or may be prepared according to methods disclosed in the literature.

B. Compounds of the formula I wherein $R^7$ and $R^8$ represent a hydrogen atom and $R^6$ is an alkyl group can be prepared via the following route ($R^1$, $R^2$, $R^3$, $R^4$ and $R^5$ have the previously given definitions):

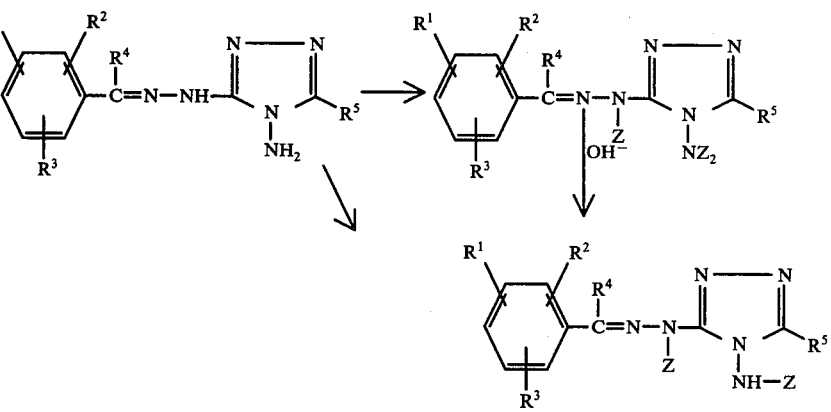

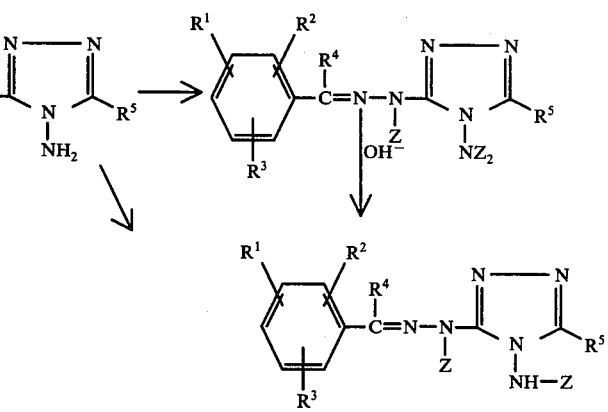

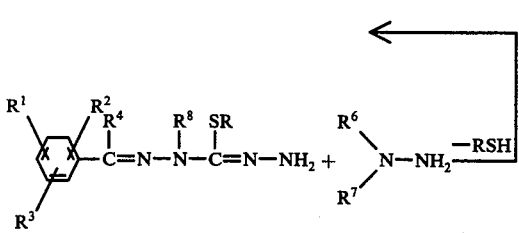

(Z = a N-protecting group, such as an arylsulphonyl group, an alkyl-sulphonyl group, an acyl group or an alkoxycarbonyl group).

The amides in the scheme above are prepared from the corresponding amines. The reaction involves the acylation of the amine or amine salt with e.g. chloroformic esters, sulphonyl halides, acyl halides or acid anhydrides.

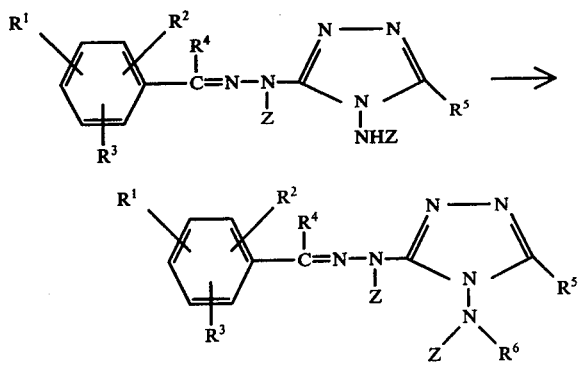

The amides are treated with an alkyl halide or a dialkyl sulphate. The reaction is preferably performed in a suitable solvent such as ethanol or water and in the presence of a base such as sodium hydrogen carbonate or sodium hydroxide.

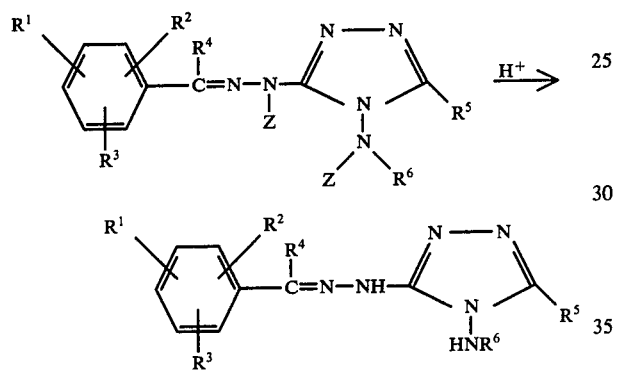

In a last step hydrolysis affords the desired compounds.

Generally, the compounds of the formula I wherein $R^6$, $R^7$ and $R^8$ are all hydrogen are prepared by treating a benzaldehyde or ketone of the formula

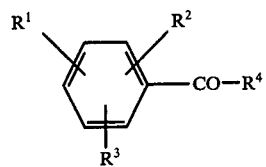
II wherein $R^1$, $R^2$, $R^3$ and $R^4$ are as previously described, with the free base or a salt of the substituted 4-amino-3-hydrazino-1,2,4-triazole of the formula

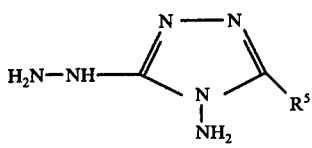
VIII wherein $R^5$ is as previously described.

The condensation is performed essentially as described in the literature (Ann. 664, 147 (1963); J. Org. Chem. 30, 711 (1965); Acta Pharm. Suecica 7, 87 (1970). The reaction is carried out at elevated temperatures in a suitable solvent such as ethanol, preferably in acid pH. The aldehydes may not be isolated, but treated in situ with triazoles of formula VIII. In weak HCl-medium I is formed as the hydrochloride. Other salts which may be used include the strong mineral acid salts, e.g. the hydrogen halides or sulphate and the like. The resulting product is readily recovered by conventional techniques, e.g. filtration. The acid addition salt may be converted to the free base by standard methods. The intermediates of formula II and VIII are known or may be prepared according to standard methods (Ann. 664, 147 (1963); J. Org. Chem. 30, 711 (1965); Acta Pharm. Suecica 9, 513 (1972).

Compounds of the formula I wherein $R^5$, $R^6$, $R^7$ and $R^8$ are hydrogen atoms can also be prepared by treating a compound of the formula

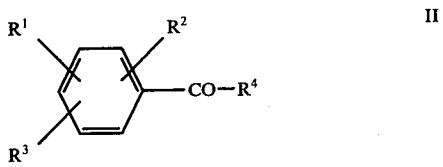
II wherein $R^1$, $R^2$, $R^3$ and $R^4$ are as previously described with a salt of triaminoguanidine in boiling formic acid.

(e) Working Examples

This invention is further illustrated by the following examples.

EXAMPLE 1

4-Acetamido-3[1-acetyl-2-(2,6-dichlorobenzylidene)-hydrazino]-1,2,4-triazole

ALTERNATIVE A

To a warm solution (~45° C) of 46.0 g of 4-amino-3-(2,6-dichlorobenzylidenehydrazino)-1,2,4-triazole hydrochloride in 150 ml of dry pyridine is added dropwise while stirring 25 ml of acetyl chloride. The mixture is stirred overnight at room temperature and is then poured into 1 liter of ice water. The precipitate formed is collected by filtration and washed with water.

Yield: 43.5 g, m.p. 205°-210°.

The crude product is recrystallized from dilute dioxane yielding 31.6 g of the compound, melting at 211°-212°.

Calculated for $C_{13}H_{12}Cl_2N_6O_2$: C, 43.96, H, 3.41, Cl, 19.95, N, 23.66, O, 9.01. Found: C, 44.0, H, 3.43, Cl, 20.1, N, 23.8, O, 8.95.

ALTERNATIVE B

To a stirred suspension of 15 g of 4-diacetylamino-3-[1-acetyl-2-(2,6-dichlorobenzylidene)hydrazino]-1,2,4-triazole in a mixture of 100 ml of ethanol and 200 ml of water is added 50 ml of saturated sodium carbonate solution. The stirred mixture is heated in a boiling water bath for 10 minutes. The obtained solution is diluted with water to a volume of 1 liter and is then acidified with acetic acid. The precipitate is filtered off and washed with water.

Yield: 8.1 g, m.p. 209°-211°.

The crude compound is recrystallized from dilute dioxane yielding 6.0 g of the compound, melting at 211°-212°.

4-Diacetylamino-3-[1-acetyl-2-(2,6-dichlorobenzylidene) hydrazino]-1,2,4-triazole A solution of 30.8 g of 4-amino-3-(2,6-dichlorobenzylidene-hydrazino)-1,2,4-triazole hydrochloride in 100 ml of acetic anhydride is heated at reflux temperature for 1.5 hours. After cooling 600 ml of water is added. The mixture is then stirred at room temperature for 2 hours. The obtained precipitate is collected and washed with water. Yield: 35.6 g, m.p. 140°–150°. The product is recrystallized from diluted ethanol.

Yield: 15.1 g, m.p. 178°–179°.

Calculated for $C_{15}H_{14}Cl_2N_6O_3$; C, 45.36, H, 3.55, Cl, 17.85, N, 21.16, O, 12.08. Found: C, 44.9, H, 4.08, Cl, 17.8, N, 20.9, O, 12.1.

4-(N-Methylacetamido)-3-[1-acetyl-2-(2,6-dichlorobenzylidene)-hydrazino]-1,2,4-triazole To a solution of 31.5 g of 4-acetamido-3-[1-acetyl-2-(2,6-dichlorobenzylidene) hydrazino]-1,2,4-triazole and 53.0 g of sodium carbonate in 400 ml of water is added dropwise, while stirring and cooling in an ice bath, 40 ml of dimethyl sulphate (2 h). After the addition the mixture was stirred for 2.5 h while cooling in ice and left overnight at room temperature. The obtained precipitate is collected and recrystallized twice from dioxane-isopropyl ether.

Yield: 7.3 g, m.p. 167°–169°.

Calculated for $C_{14}H_{14}Cl_2N_6O_2$; C, 45.54, H, 3.82, Cl, 19.20, N, 22.76, O, 8.67. Found C, 45.8, H, 4.07, Cl, 19.2, N, 22.7, O, 9.01.

3-(2,6-Dichlorobenzylidenehydrazino)-4-methylamino-1,2,4-triazolehydrochloride A solution of 6.2 g of 4-(N-Methylacetamido)-3-[1-acetyl-2-(2,6-dichlorobenzylidene)hydrazino]-1,2,4-triazole in 50 ml of acetic acid, 50 ml of concentrated hydrochloric acid and 50 ml of water is heated at reflux overnight. The solution is evaporated and the residue is recrystallized from ethanolisopropyl ether.

Yield 2.4 g, m.p. 205°–207°. Two more recrystallizations from the same solvent mixture gave 1.5 g of an analytically pure sample, m.p. 210°–211°.

Calculated for $C_{10}H_{10}Cl_2N_6 \cdot HCl$: C, 37.34, H, 3.45, Cl, 33.07, N, 26.13. Found: C, 37.5, H, 3.56, Cl, 33.3, N, 25.7.

EXAMPLE 2

1-[2,6-dichlorobenzylidene]-5,5-dimethyl-thiocarbohydrazine 5.4 g of 1,1-dimethylthiocarbohydrazine and 7.1 g of 2,6-dichlorobenzaldehyde was refluxed in 100 ml of dry ethanol for 18 hours. The reaction mixture was cooled, and the solid precipitate was filtered off. Yield 7.3 g. M.p. 205° C.

1-[2,6-dichlorobenzylidene]-5,5,5-trimethylisothiocarbohydrazine 7.3 g of 1-[2,6-dichlorobenzylidene]-5,5-dimethylthiocarbohydrazine and 3.5 g of $CH_3I$ in 50 ml of dry ethanol is refluxed for 2 hours. The reaction mixture is evaporated, ether is added and the crystalline residue filtered. Yield 5.2 g of a low melting solid (<50° C).

1-[2,6-dichlorobenzylidene]-2-dimethylamino-3-aminoguanidine 0.6 g of hydrazinehydrate and 5 g of 1[2,6-dichlorobenzylidene]-5,5,5-trimethylisothiocarbohydrazine were dissolved in 50 ml of dry ethanol and stirred for 18 hours. The solvent is evaporated and water added. pH is adjusted to 8–10 and the precipitate is filtered. It is then dissolved in HCl-acid, the excess of which is evaporated. Yield 2.6 g. M.p. 183° C.

3-[2,6-dichlorobenzylidenehydrazino]-4-dimethylamino-1,2,4-triazole 2.5 g of 1-[2,6-dichlorobenzylidene]-2-dimethylamino-3-aminoguanidine is dissolved in 25 ml of 85% formic acid for one hour. The mixture is evaporated and the residue dissolved in 25 ml 6 N HCl-acid and refluxed for another 30 min. The reaction mixture is evaporated and the residue recrystallized. Yield 1 g. M.p. 189° C.

EXAMPLE 3

4-Amino-3-(2-methylbenzylidenehydrazino)-1,2,4-triazole hydrochloride (Compound I in Table 1).

To a solution of 14.0 g (0.075 mole) of 4-amino-3-hydrazino-1,2,4-triazole dihydrochloride in 200 ml of 75 percent ethanol was added 9.0 g (0.075 mole) of o-tolualdehyde. The mixture was stirred and heated at reflux for 1.5 hour. The solution was cooled and the precipitate formed collected by filtration and washed with ether. Yield: 18.4 g, m.p. 230°–232° (D). After recrystallization from aqueous ethanol-isopropyl ether the product melts at 233°–234° (D).

EXAMPLE 4

(a)

4-Amino-3-(2,6-dichlorobenzylidenehyrazino)-1,2,4-triazole hydrochloride (Compound VI in Table 1)

Method 1

To a solution of 7.5 g (0.04 mole) of 4-amino-3-hydrazino-1,2,4-triazole dihydrochloride in 150 ml of 75 percent ethanol was added 7.0 g (0.04 mole) of 2,6-dichlorobenzaldehyde. The mixture was stirred and heated at reflux for 16 hours. The solution was cooled and the crystallization was brought about by the addition of ether. The precipitate was filtered off and washed with ether.

Yield: 10.2 g, m.p. 219°–220° (D).

38.0 g of the hydrochloride yielded when treated with 17.0 g sodium hydrogen carbonate in 1000 ml of water, 28.2 g (84%) of the free base, melting at 198°–199°.

Equivalent weight: Calc. 271.12, found 273.

The free base was converted to the bisulphate salt by dissolving 8.5 g of the base in 50 ml of acetic acid and treating the solution with 10 ml of concentrated sulphuric acid. 400 ml of ether was added and the obtained precipitate (10.4 g) was recrystallized from ethanol-isopropyl ether yielding 4.5 g of the pure salt, melting at 208°–209° (D), anal. calc. for $C_9H_9Cl_2N_6 \cdot H_2SO_4$: C, 29.28, H, 2.73, N, 22.76, S, 8.69. Found: C, 28.7, H, 2.9, N, 22.5, S, 8.6.

(b)

4-Amino-3-(2,6-dichlorobenzylidenehydrazino)-1,2,4-triazole hydrochloride (Compound VI in Table 1).

Method 2

To a solution of 7.0 g (0.05 mole) triaminoguanidine hydrochloride in a mixture of 50 ml of formic acid and 10 ml of water was added 8.5 (0.049 mole) of 2,6-dichlorobenzaldehyde. The mixture was stirred and refluxed for 6 hours. 40 ml of concentrated hydrochloric acid was then added and the mixture was refluxed for 0.5 hour. The solution was evaporated under reduced pressure and the residue was recrystallized from ethanol-isopropyl ether.

Yield: 12.2 g (82%) m.p. 217°–218° (D). One more recrystallization from the same solvent gave 9.7 g of an analytically pure sample, m.p. 218°–219° (D).

EXAMPLE 5

4-Amino-3-(2,6-dichlorobenzylidenehydrazino)-5-methyl-1,2,4-triazole hydrochloride (Compound VII in Table 1)

To a solution of 5.25 g (0.032 mole) of 4-amino-3-hydrazino-5-methyl-1,2,4-triazole hydrochloride in 100 ml of 75 percent ethanol was added 5.6 g (0.032 mole) of 2,6-dichlorobenzaldehyde and 0.5 ml of concentrated hydrochloric acid. The mixture was stirred and heated at reflux for 16 hours. After cooling, the precipitate was collected and washed with chilled ethanol and ether. Yield: 7.0 g, m.p. 244°–245° (D).

EXAMPLE 6

4-Amino-3-(2,6-dimethylbenzylidenehydrazino)-1,2,4-triazole hydrochloride (Compound II in Table 1)

In an atmosphere of dry nitrogen, a solution of 9.25 g (0.05 mole) of 2,6-dimethylbromobenzene in 100 ml of ether was added dropwise with stirring to 1.2 g (0.05 g atom) of magnesium turnings in 20 ml of ether. The reaction was started by the addition of ethyl bromide and a crystal of iodine. when all the halide had been added, the solution was refluxed for 2 hours. 8.2 ml (0.052 mole) of triethyl orthoformate was added dropwise and the reaction mixture was refluxed for 1.5 hour and left overnight at room temperature. To the solution was added dropwise while stirring and cooling a mixture of 50 ml of concentrated hydrochloric acid and 50 ml of water. The stirring was continued for 30 minutes. The ether layer was separated and the ether removed by evaporating. To the residue was added a solution of 9.35 g (0.05 mole) 4-amino-3-hydrazino-1,2,4-triazole dihydrochloride in 130 ml of 75 percent ethanol. The mixture was stirred and heated at reflux for 5 hours. 6000 ml of ethanol was added and the solution cooled. After filtration and evaporation of the solvent 3.6 g of the crude salt was obtained. After recrystallization from ethanol-2N hydrochloric acid, the product melts at 219°–220° (D).

In Table 1 are given data for some compounds of this invention including those described in Examples 3–6.

Table 1

| | 4-amino-3-benzylidenehydrazino-1,2,4-triazole hydrochloride ($R^6$, $R^7$, $R^8$ all hydrogen) | | | | | | | | | | | |
|---|---|---|---|---|---|---|---|---|---|---|---|---|
| Compound No | $R_1$ | $R_2$ | $R_3$ | $R_4$ | $R_5$ | Reaction time h | M.P. °C | Yield % | Analysis: calc % found % | | | |
| | | | | | | | | | C | H | N | Cl |
| I | 2-CH$_3$ | H | H | H | H | 1.5 | 233–34 | 97 | 47.72 47.7 | 4.81 4.9 | 33.39 33.5 | 14.09 14.0 |
| II | 2-CH$_3$ | 6-C$_3$ | H | H | H | 5 | 219–20 | 27 | 49.53 49.3 | 5.67 5.78 | 31.51 31.2 | 13.29 13.1 |
| III | 2-CH$_3$ | 4-CH$_3$ | 6-CH$_3$ | H | H | 3 | 218–19 | 57 | 51.33 51.2 | 6.10 6.3 | 29.93 29.4 | 12.63 12.7 |
| IV | 2-Cl | H | H | H | H | 0.5 | 24–50 | 92 | 39.58 39.5 | 3.69 3.70 | 30.77 30.4 | 25.96 26.8 |
| V | 2-Cl | 4-Cl | H | H | H | 2.5 | 270–271 | 89 | 35.14 35.4 | 2.95 2.94 | 27.33 27.1 | 34.58 34.6 |
| VI | 2-Cl | 6-Cl | H | H | H | 16 | 219–20 | 83 | 35.14 34.8 | 2.95 3.05 | 27.33 27.3 | 34.58 34.4 |
| VII | 2-Cl | 6-Cl | H | H | CH$_3$ | 16 | 244–45 | 68 | 37.34 37.3 | 3.45 3.33 | 26.13 25.9 | 33.07 33.2 |
| VIII | 2-Cl | 6-Cl | H | H | C$_2$H$_5$ | 16 | 224–25 | 56 | 39.38 39.4 | 3.90 3.96 | 25.04 25.1 | 31.69 31.4 |
| IX[a)] | H | H | H | N | H | 2 | 220–21 | 65 | 45.41 45.2 | 4.63 4.79 | 26.48 26.0 | 19.15 19.0 |

[a)]The compound was obtained as a dihydrochloride monohydrate, Cal.: 0 4.32, Found: 0 4.49.

EXAMPLE 7

4-Amino-3-[α-(2-pyridyl)benzylidenehydrazino]-1,2,4-triazole dihydrochloride monohydrate To a solution of 5,6 g (0,03 mole) of 4-amino-3-hydrazino-1,2,4-triazole dihydrochloride in 15 ml of water, 50 ml of ethanol and some drops of concentrated HCl 5,5 g (0.03 mole) of 2-benzoylpyridine was added. The mixture was refluxed for 3 hours. The obtained precipitate was collected and washed with ether. M.p. 218°–220° C (D). Yield 7,2 g (65%). After recrystallization from diluted ethanol the product melted at 220°–221° C (D). Yield: 4,7 g.

Analysis, calculated for C$_{14}$H$_{13}$N$_7$ · 2HCl · H$_2$O: C, 45.41, H, 4.63, Cl, 19.15, N, 26.48, O, 4.32. Found: C, 45.2, H, 4.79, Cl, 19.0, N, 26.0 O, 4.49.

In the same way as described above the following compounds were prepared

| R¹ | R² | R³ | R⁴ | Reaction time (h) | M.P. °C | Yield % | Analysis Calculated % found % | | | | |
|---|---|---|---|---|---|---|---|---|---|---|---|
| | | | | | | | C | H | H | Cl | O |
| H | H | H | (3-pyridyl) | 4 | 203–204 | 71 | 47.73<br>47.1 | 4.29<br>4.58 | 27.84<br>27.5 | 20.13<br>20.2 | |
| H | H | H | (4-pyridyl) | 4 | 234–235 | 81 | 47.73<br>47.0 | 4.29<br>4.63 | 27.84<br>27.9 | 20.13<br>20.1 | |
| 2-Cl | H | H | (4-pyridyl) | 16 | 233–234 | 74 | 43.48<br>43.2 | 3.65<br>3.71 | 25.4<br>25.1 | 27.51<br>27.1 | |
| 4Cl | H | H | (4-pyridyl) | 16 | 175–177 | 68 | 40.64<br>40.7 | 4.14<br>4.24 | 23.70<br>23.6 | 25.71<br>25.5 | 5.80ᵃ<br>6.30 |
| 4-Cl | H | H | (2-pyridyl) | 3.5 | 228–229 | 55 | 43.48<br>43.9 | 3.65<br>3.75 | 25.40<br>25.3 | 27.50<br>27.3 | |

ᵃCalculated: H₂O 6.53; found 6.8

(f) Biological Tests

A comparison of the pharmacological effects of the compound of the invention with the designation FLA 136 having the formula

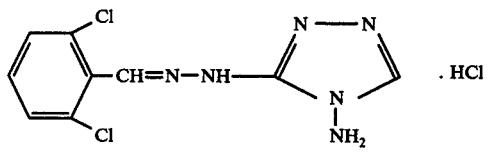

with those of Wy-8678, a well-known hypotensive agent [Experientia (Basel) 25, 1066 (1969)], is presented in Table 2.

The hydrochloride salt of Wy-8678, which is used in the tests described below has the formula

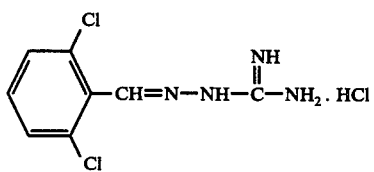

The antihypertensive effects were tested in rats in which high blood pressure had been produced by removal of one kidney and restricting the blood flow to the remaining one two months before the experiments. The animals were prepared for measurements of the arterial blood pressure through a catheter implanted into the abdonimal aorta and exteriorized at the base of the neck. Groups of two rats were given three consecutive daily oral doses of the test compounds from the scale: 2.5, 5, 10, 20, and 40 mg/kg. Measurements were performed before and three hours after administration to the unanaesthetized animal. The minimum daily oral dose with antihypertensive effect was defined as the dose which reduced the mean arterial blood pressure more than 15 mm Hg. It can be seen from Table 2 that the antihypertensive effect of the test compound of the invention is of the same degree as that of one of the present known most active hypotensive compounds.

The effect on the spontaneous motor activity was tested in mice. Groups of six animals were given the test compounds intraperitoneally one and three hours before test. The animals were placed individually in an activity meter and the activity was recorded for ten minutes. The dose which reduced the spontaneous motor activity to 50 percent of that of control mice was calculated. The lack of sedative effects of the test compound of the invention as compared to Wy-8678 is evident from Table 2.

Intravenous administration of consecutive increasing doses of the test compound of the invention and Wy-8678 to anaesthetized rats showed that the test compound of the invention did not produce an initial rise in blood pressure even at 40 mg/kg which was the highest dose tested. Wy-8678 on the other hand produced a large increase in arterial pressure even at doses as low as 0.01 mg/kg.

Table 2.

Pharmacological effects of 4-amino-3-(2,6-dichlorobenzylidenehydrazino)-1,2,4-triazole hydrochloride (FLA 136), a compound according to the invention, and Wy-8678, a reference substance

| | FLA 136 (mg/kg) | Wy-8678 (mg/kg) |
|---|---|---|
| Minimum daily oral dose with antihypertensive effects defined as the dose which reduced the mean arterial blood pressure more than 15 mm Hg in unanaesthetized renal hypertensive rats | 2.5–5 | 2.5 |
| Acute toxicity in mice (LD$_{50}$ i.p.) | 340 | 70 |
| The intraperitoneal dose which reduced the spontaneous motor activity of mice to 50 % of control values | | |
| a) measurements one hour after administration | 90 | 3 |
| b) measurements three hours after administration | 170 | 3 |

The antihypertensive effects of the hydrochloride salt of the compound of the invention with the designation FLA 486 having the formula

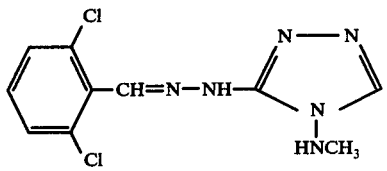

have been compared with those of FLA 136 with the formula

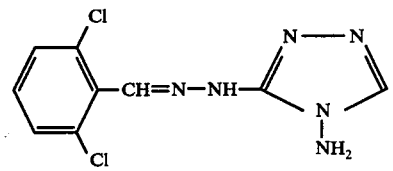

in spontaneously hypertensive rats of the SHR/N strain (Möllegaard Hansens Avlslaboratorier A/S, Denmark). The animals were prepared for measurements of the arterial blood pressure through a catheter implanted into the abdominal aorta and exteriorized at the base of the neck. Groups of two rats were given three consecutive daily oral doses of the test compounds. Measurements were performed before and three hours after administration to the unanesthetized animal. The effective antihypertensive dose of FLA 486, defined as the dose which reduced the mean arterial blood pressure more than 30 mm Hg was 5–10 mg/kg. The corresponding value for FLA 136 was 5–10 mg/kg.

We claim:

1. A compound of the formula

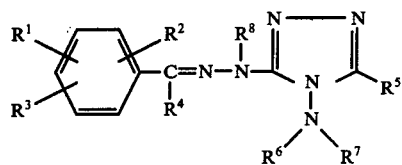

or a pharmaceutically acceptable salt thereof wherein $R^1$, $R^2$ and $R^3$ are the same or different and each represents a hydrogen atom, a lower alkyl group or a halogen atom, $R^4$ represents a pyridyl group, and $R^5$, $R^6$, $R^7$ and $R^8$ are the same or different and each represents a hydrogen atom or a lower alkyl group.

2. A compound according to claim 1 characterized by the formula I, or a pharmaceutically acceptable salt thereof, in which formula $R^6$, $R^7$ and $R^8$ are not all simultaneously hydrogen atoms.

3. A compound according to claim 1 characterized by the formula I, or a pharmaceutically acceptable salt thereof, in which formula $R^5$ represents a hydrogen atom or a lower alkyl group, and $R^6$, $R^7$ and $R^8$ represent hydrogen atoms.

4. A compound according to claim 3 characterized by the formula I, or a pharmaceutically acceptable salt thereof, in which formula $R^5$ represents a hydrogen atom.

5. A hypotensive pharmaceutical preparation which comprises as active ingredient a therapeutically effective amount of at least one compound according to claim 1, or a pharmaceutically acceptable salt thereof, in association with a pharmaceutically acceptable carrier.

6. A hypotensive pharmaceutical preparation which comprises as active ingredient a therapeutically effective amount of at least one compound according to claim 2, or a pharmaceutically acceptable salt thereof, in association with a pharmaceutically acceptable carrier.

7. A hypotensive pharmaceutical preparation which comprises as active ingredient a therapeutically effective amount of at least one compound according to claim 3, or a pharmaceutically acceptable salt thereof, in association with a pharmaceutically acceptable carrier.

8. A hypotensive pharmaceutical preparation which comprises as active ingredient a therapeutically effective amount of at least one compound according to claim 4, or a pharmaceutically acceptable salt thereof, in association with a pharmaceutically acceptable carrier.

9. A method for the treatment of hypertension, comprising administering to a host suffering from such ailment a therapeutically effective amount of a compound according to claim 1 or a pharmaceutically acceptable salt thereof.

10. A method for the treatment of hypertension, comprising administering to a host suffering from such ailment a therapeutically effective amount of a compound according to claim 2 or a pharmaceutically acceptable salt thereof.

11. A method for the treatment of hypertension, comprising administering to a host suffering from such ailment a therapeutically effective amount of a compound according to claim 3 or a pharmaceutically acceptable salt thereof.

12. A method for the treatment of hypertension, comprising administering to a host suffering from such ailment a therapeutically effective amount of a compound according to claim 4 or a pharmaceutically acceptable salt thereof.

* * * * *